United States Patent [19]

Fruchey

[11] Patent Number: 4,973,752
[45] Date of Patent: * Nov. 27, 1990

[54] NOVEL PROCESS TO PREVENT FORMATION OF CHLORINATED BY-PRODUCTS IN APAP PRODUCTION

[76] Inventor: Olan S. Fruchey, 2310 Raintree, Corpus Christi, Tex. 78409

[*] Notice: The portion of the term of this patent subsequent to Aug. 8, 2006 has been disclaimed.

[21] Appl. No.: 342,914

[22] Filed: Apr. 24, 1989

Related U.S. Application Data

[63] Continuation-in-part of Ser. No. 118,117, Nov. 6, 1987.

[51] Int. Cl.$^5$ .................. C07C 233/25; C07B 43/06
[52] U.S. Cl. .................................................. 564/223
[58] Field of Search ...................................... 564/223

[56] References Cited

U.S. PATENT DOCUMENTS

| 4,524,217 | 6/1985 | Davenport et al. | 564/223 |
| 4,560,789 | 12/1985 | Davenport et al. | 564/223 X |
| 4,568,763 | 2/1986 | Davenport et al. | 564/223 X |
| 4,855,499 | 8/1989 | Fruchey | 564/223 |

OTHER PUBLICATIONS

Donaruma et al., Organic Reactions, vol. II, Chapter I, pp. 1-157 (1960).

Primary Examiner—Carolyn S. Elmore
Attorney, Agent, or Firm—Marvin Turken; Herbert M. Hanegan

[57] ABSTRACT

A novel process is disclosed for the prevention of the formation of chlorinated by-products during the Beckmann rearrangement of 4-hydroxyacetophenone oxime to APAP utilizing thionyl chloride as catalyst, by the addition of an inorganic iodide such as potassium iodide to the Beckmann rearrangement reactor.

14 Claims, No Drawings

NOVEL PROCESS TO PREVENT FORMATION OF CHLORINATED BY-PRODUCTS IN APAP PRODUCTION

CROSS-REFERENCE TO RELATED APPLICATION

This application is a continuation-in-part of application Ser. No. 118,117, filed Nov. 6, 1987.

BACKGROUND OF THE INVENTION

This invention relates to a novel process for the prevention of chlorinated by-products in the production of N-acetyl-para-aminophenol (APAP) by the Beckmann rearrangement of 4-hydroxyacetophenone oxime using thionyl chloride as the catalyst.

U.S. Pat. No. 4,524,217, the entire disclosure of which is herein incorporated by reference, describes a novel process for the preparation of N-acyl-hydroxy aromatic amines in general and specifically N-acetyl-para-aminophenol (APAP), by reacting a hydroxy aromatic ketone such as 4-hydroxyacetophenone with a hydroxylamine salt and a base to obtain the ketoxime of the ketone, e.g., 4-hydroxyacetophenone (4-HAP) oxime and then subjecting the oxime to a Beckmann rearrangement in the presence of a catalyst to form said N-acyl-hydroxy aromatic amines. Thionyl chloride in liquid sulfur dioxide is disclosed as a catalyst.

U.S. patent application Ser. No. 118,117, filed Nov. 6, 1987, discloses and claims a process of carrying out the Beckmann rearrangement of 4-HAP oxime to APAP utilizing thionyl chloride as a catalyst in liquid sulfur dioxide as solvent, wherein an inorganic iodide, e.g., potassium iodide is added to minimize the formation of chlorinated by-products.

Pending Fruchey et al. U.S. patent application Ser. No. 217,652 filed July 12, discloses and claims the use of an alkyl alkanoate as solvent for the thionyl chloride catalyst in carrying out the Beckmann rearrangement of 4-HAP oxime to APAP. Also disclosed and claimed is the addition of an alkali metal iodide such as potassium iodide to the reaction to minimize the formation of undesirable by-products. The entire disclosure of this application is incorporated by reference.

Although the process for the production of APAP as set forth in U.S. Pat. No. 4,524,217 is very effective, it has been found that a certain chlorinated by-product is formed during the Beckmann rearrangement of the 4-hydroxyacetophenone oxime when using said thionyl chloride as the Beckmann rearrangement catalyst. The chlorinated by-product which is formed during said Beckmann rearrangement is 3-chloro-4-hydroxyacetanilide (CAPAP). CAPAP is merely APAP chlorinated in the 3 position and although the exact mechanism for its formation has not yet been determined, it was discovered as a trace impurity in the crude APAP from the Beckmann reactor and also in the final product.

Although the 3-chloro-4-hydroxyacetanilide which is formed during the Beckmann rearrangement of 4-hydroxyacetophenone oxime when using thionyl chloride as catalyst is not known to have any detrimental effects, there is some indication that 3-chloro-4-hydroxyacetanilide affects the color of the APAP over a period of time. Nevertheless, experiments are inconclusive and are affected by the manner in which APAP is purified, either a single or double crystallization, etc. However, as can well be appreciated by those skilled in the art, APAP is an important commodity of commerce being one of the most widely used over-the-counter analgesics. It goes without saying that for human consumption, this product should be as pure as possible and chlorinated by-products are definitely not desirable.

SUMMARY OF THE INVENTION

It has now been found that the formation of chlorinated by-products during the Beckmann rearrangement of 4-hydroxyacetophenone oxime in the presence of thionyl chloride as catalyst can be almost entirely eliminated by incorporating a small amount of an inorganic iodide such as sodium iodide or potassium iodide. It is to be noted that insofar as the chemistry of the reaction is concerned, other inorganic iodides can be used but since potassium iodide is already approved as the iodide source in iodized table salt, it should pose no health risk in APAP and therefore is the preferred iodide salt.

The novel process of this invention is carried out simply by adding an alkali metal iodide such as potassium iodide to the 4-hydroxyacetophenone oxime prior to carrying out the Beckmann rearrangement in the presence of said thionyl chloride. The amount of metal iodide utilized is extremely small and very acceptable results have been obtained when using 0.2 wt.% of potassium iodide relative to the oxime. It should be realized that no particular advantage is gained in going over the 0.2 gram per 100 grams of 4-hydroxyacetophenone oxime but, obviously, such can be done if desired. The amount of inorganic iodide which should be added is that amount sufficient to substantially prevent the formation of chlorinated by-products and said amount is usually in the range varying from 0.02 gram to 2.0 grams of potassium iodide per 100 grams of 4-hydroxyacetophenone oxime which is subjected to the Beckmann rearrangement.

Although it is possible to carry out the process of this invention in the absence of a solvent for the thionyl chloride, such solvent is preferred in most embodiments for the purpose of controlling the heat of reaction. Some appropriate solvents are for example liquid sulfur dioxide; esters such as $C_1$-$C_6$ alkyl esters of alkanoic acids having 2 to 6 carbon atoms, e.g., ethyl acetate, isopropyl acetate, butyl acetate, n-hexyl acetate, and methyl n-hexanoate; ethers such as tetrahydrofuran and diethyl ether; ketones such as acetone; nitroethane; and mixtures of any of the foregoing solvents. The preferred solvent is liquid sulfur dioxide.

It should be immediately understood that the manner in which iodide is added to the Beckmann rearrangement reactor is by no means critical and it can be added directly to the reactor or it can be contained in a recycle stream such as the solvent. In fact, as will be demonstrated in some of the examples when liquid $SO_2$ is, the solvent, it is not necessary to add iodide for every single run since some of the iodide initially added is present in the recycle $SO_2$ stream, and experiments to date have indicated that when the $SO_2$ containing potassium iodide was recycled to a reactor into which fresh 4-hydroxyacetophenone oxime, thionyl chloride and make-up $SO_2$ were added, a total of four cycles could be carried out without the reappearance of 3-chloro-4-hydroxyacetanilide (CAPAP). Thus, this suggests that, commercially, the iodide would only be added to the first batch of a recycle series and any iodide make-up added if and when production of CAPAP reappeared.

For reasons which are not completely understood, it appears that the presence of an inorganic iodide in the Beckmann reactor not only eliminates CAPAP production but also decreases other unknowns typically present in the reactor product. While not wishing to be bound by any theory of operation, it appears that the action of the iodide on other unknowns is reasonable if one assumes that these other unknowns are APAP oxidation products. The iodide can act as a sink for any oxidizing potential in the reactor. Also, chlorine is a known oxidizing agent and by removing the chlorine, the iodide prevents not only chlorination but oxidation from occurring. The Beckmann rearrangement of 4-hydroxyacetophenone oxime utilizing sulfur dioxide and thionyl chloride is disclosed in U.S. 4,524,217.

The reaction can be carried out at any convenient temperature ranging from about 0° to 35° C. for a period of time ranging from 15 minutes to about 4 hours. The pressure is not narrowly critical and may be, for example, in the range of 80 millimeters of mercury to 10 atmospheres absolute. The amount of thionyl chloride utilized in relation to the 4-hydroxyacetophenone oxime is also not narrowly critical. The weight ratio of oxime to thionyl chloride may range, for example from about 5:1 to 300:1, preferably about 250:1 to 100:1. However, the solubility of APAP in a solvent such as liquid sulfur dioxide increases as the thionyl chloride level increases. This increased solubility obviously affects product recovery. Thus, the least amount of thionyl chloride should be used in order to maximize product recovery.

The following examples will illustrate the best mode contemplated for carrying out the novel process of this invention.

EXAMPLES 1 to 24

In all the examples which follow, the experimental procedure which was used is as follows:

(1) An appropriate 1 liter Zipperclave liner was charged with 100 grams of 4-HAP oxime and 0.2 gram KI (if a KI run). The liner was placed in a reactor and the reactor sealed.
(2) The reactor was cooled to 50° C. with dry ice/acetone bath and 500 grams of sulfur dioxide charged via vacuum transfer.
(3) At −50° C., 0.7 ml of thionyl chloride were added via a syringe.
(4) The contents of the reactor were warmed via a water bath to room temperature and the reaction exotherm was not allowed to exceed 30° C. Temperature control was achieved by venting $SO_2$.
(5) The contents of the reactor were allowed to stand at room temperature for 30 minutes; no stirring was employed during the entire course of the run.
(6) The reactor contents were then cooled to −50° C. and the resulting slurry poured into the appropriate liner for flashing $SO_2$.
(7) The liner was placed back in the reactor and the contents warmed to 30° C.
(8) After standing for 30 minutes at room temperature, the $SO_2$ was flashed off.
(9) The solids were placed in the appropriate slurry neutralization vessel which contained 250 ml of demineralized water and 0.1 gram of sodium dithionite.
(10) The pH of the slurry was adjusted to 6 with a 20% caustic solution.
(11) The slurry was filtered and the solids washed with 100 ml of demineralized water.
(12) A sample of the solids was dried in a vacuum oven at 60° C. overnight and then submitted for high performance liquid chromatography analysis.

The following tables will illustrate the results obtained utilizing the above-described procedures.

In Table I, the column "Reactor Liner" refers to the Zipperclave liner utilized in steps (1) through (5). The "Flasher Liner" refers to the liner used in steps (7) and (8). In all cases, the slurry neutralization vessel, i.e., steps (9) through (11), was 316 stainless steel.

TABLE I

| Example | Reactor Liner* | Flasher Liner | KI Present | CAPAP (PPM) | Unknowns (PPM) |
|---|---|---|---|---|---|
| 1 | 316SS | 316SS | No | 700 | 114 |
| 2 | 316SS | 316SS | Yes | ND*** | 71 |
| 3 | 316SS | 316SS | No | 270 | 126 |
| 4 | 316SS | 316SS | Yes | ND | 45 |
| 5 | 316SS | 316SS | No | 900 | 122 |
| 6 | 316SS | 316SS | Yes | ND | 88 |
| 7 | Glass | 904L | No | 620 | 94 |
| 8 | Glass | 904L | Yes | ND | 39 |
| 9 | Glass | 904L | No | 930 | 94 |
| 10 | Glass | 904L | Yes | ND | 58 |
| 11 | Glass | 904L | No | 1300 | 129 |
| 12 | Glass | 904L | Yes | ND | 51 |
| 13 | 904L** | 904L | No | 490 | 116 |
| 14 | 904L | 904L | Yes | ND | 44 |
| 15 | 904L | 904L | No | 200 | 99 |
| 16 | 904L | 904L | Yes | ND | 69 |
| 17 | 904L | 904L | No | 170 | 144 |
| 18 | 904L | 904L | Yes | ND | 53 |
| 19 | Teflon | 904L | Yes | ND | 59 |
| 20 | Teflon | 904L | No | 180 | 98 |
| 21 | Teflon | 904L | Yes | ND | 21 |
| 22 | Teflon | 904L | No | 106 | 71 |
| 23 | Teflon | 904L | Yes | ND | 21 |
| 24 | Teflon | 904L | No | 235 | 93 |

*In the case of the glass reactor metallurgy a Co-glass coupon was placed in a Teflon liner.
**904L is high grade stainless steel.
***None detected.

From Table I, it can be seen that four sets of six experiments each were carried out using four different reactor liners and two different flasher liners. The results show that, irrespective of the reactor liner or the flasher liner, potassium iodide reduced the levels of CAPAP to such an extent that they were not detectable. As can be seen, unknowns were also reduced utilizing potassium iodide.

EXAMPLES 25 to 28

These examples illustrate the recycle iodide effect.

The procedure that was followed was the same as that set forth for the previous examples with the exception that no new potassium iodide was added but only the amount that was contained in the recycle $SO_2$ stream was used. Thus, in step (1) of the experimental procedure previously set forth, no KI was added (after the initial run) and in step (2), the sulfur dioxide was from a preceding run and contained residual KI. The flashing of $SO_2$ was not carried out for Examples 25-27 but the reactor slurry was filtered and the $SO_2$ recycled to step (2). For Example 28, the $SO_2$ was flashed. The recycle was carried out for four separate cycles with the following results shown in Table II.

TABLE II

| Example | Recycle Number | CAPAP (PPM) | Unknowns (PPM) |
|---|---|---|---|
| 25 | 1 | ND* | 14 |
| 26 | 2 | ND | 35 |
| 27 | 3 | ND | 116 |

TABLE II-continued

| Example | Recycle Number | CAPAP (PPM) | Unknowns (PPM) |
|---------|----------------|-------------|----------------|
| 28 | 4 | ND | 118 |

*ND = None detected.

As can be seen, a total of four cycles were run and absolutely no CAPAP was detected. These examples illustrate the fact that fresh potassium iodide need not be added at every single run but only upon the appearance of undesirable by-products.

EXAMPLE 29

This example illustrates the use of an alkyl aklanoate, viz., ethyl acetate, as solvent for the reaction.

A slurry of 4-HAP oxime (100.00 g, 0.6617 mols) and potassium iodide (0.200 g) in ethyl acetate (185 mL) was stirred and heated to 50° C. under nitrogen (290 torr absolute total pressure). A solution of thionyl chloride (1.0 mL, 1.631 g, 13.71 mmole) in ethyl acetate (15 mL) was then added over 25 minutes to the stirred 4-HAP oxime/ethyl acetate slurry. The temperature of the reaction mixture was maintained at 50–51° C. by allowing the heat of the reaction to reflux the ethyl acetate solvent under 290 torr absolute total pressure. Within about ten minutes after the start of the thionyl chloride addition, the reaction mixture was a nearly homogeneous, light amber liquid. White solid APAP then began to precipitate. The refluxing started to subside after about 90% of the thionyl chloride had been added. After the thionyl chloride addition was completed, the reaction mixture was allowed to cool to 40° C. over about ten minutes and was then chilled in an ice bath to 3° C. The reaction slurry was filtered under nitrogen to give a cake of light yellow Beckmann reaction solids and a filtrate of yellow Beckmann reaction liquor. Residual ethyl acetate was pumped off the reaction solids at 0.025 torr and ambient temperature. The dried reaction solids were then purified by known washing, filtering and recrystallization procedures. The solid filter material used in the purification was dried under vacuum (0.025 torr) at ambient temperature to a mass 3.53 g greater than the weight of the starting filter material; this mass increase presumably was due mostly to adsorbed APAP. Throughout the entire preparation, the crude APAP solids and purified APAP solids were granular, free of tackiness, and easily handled.

The results of this example were as follows: 4-HAP oxime conversion=99.44%; APAP efficiency=98.52%; 4-HAP efficiency=1.12%; efficiency to other by-products=0.36%; and yield of purified APAP=75.75%. The purified APAP contained 0.009 wt.% of 4-HAP, 0.001 wt.% of 4-HAP oxime and 0.015 wt.% of other impurities which did not contain any detectable amount of CAPAP.

What is claimed is:

1. In the process for the production of N-acetylpara-aminophenol by the Beckmann rearrangement of 4-hydroxyacetophenone oxime using thionyl chloride as a catalyst, the improvement which comprises adding a small but effective amount of an inorganic iodide to the Beckmann rearrangement reactor in order to minimize the formation of chlorinated by-products.

2. The process of claim 1 wherein said inorganic iodide is an alkali metal iodide.

3. The process of claim 2 wherein the inorganic metal iodide is potassium iodide.

4. The process of claim 1 wherein a solvent for the reaction is present.

5. The process of claim 4 wherein the weight ratio of said oxime to thionyl chloride is about 5:1 to 300:1.

6. The process of claim 5 wherein said solvent is liquid sulfur dioxide.

7. The process of claim 5 wherein said weight ratio is about 100:1 to 250:1.

8. The process of claim 7 wherein said solvent is liquid sulfur dioxide.

9. The process of claim 4 wherein the inorganic iodide is added in an amount ranging from 0.02 to 2.0 grams per 100 grams of said 4-hydroxyacetophenone oxime.

10. The process of claim 9 wherein said inorganic iodide is an alkali metal iodide.

11. The process of claim 10 wherein said alkali metal iodide is potassium iodide.

12. The process of claim 4 wherein the amount of inorganic iodide added is about 0.2 grams per 100 grams of said 4-hydroxyacetophenone oxime.

13. The process of claim 12 wherein said inorganic iodide is an alkali metal iodide.

14. The process of claim 13 wherein said alkali metal iodide is potassium iodide.

* * * * *

UNITED STATES PATENT AND TRADEMARK OFFICE
CERTIFICATE OF CORRECTION

PATENT NO. : 4,973,752
DATED : Nov. 27, 1990
INVENTOR(S) : Olan S. Fruchey

It is certified that error appears in the above—identified patent and that said Letters Patent is hereby corrected as shown below:

Title Page: Should contain

[73] Assignee: Hoechst Celanese Corporation
Somerville, N.J.

Col. 2, Line 56, Delete "SO2 is," prior to the word "the", and insert --$SO_2$ is--.

Col. 3, Line 20, Delete "IO", after the word "to", and insert --10--.

Signed and Sealed this

Fifteenth Day of September, 1992

Attest:

DOUGLAS B. COMER

Attesting Officer

Acting Commissioner of Patents and Trademarks